(12) United States Patent
Doran et al.

(10) Patent No.: US 10,893,823 B2
(45) Date of Patent: Jan. 19, 2021

(54) METHOD AND APPARATUS FOR THE ASSESSMENT OF ELECTROPHYSIOLOGICAL SIGNALS

(71) Applicant: Diagnosys LLC, Lowell, MA (US)

(72) Inventors: Bruce Doran, Lowell, MA (US); Marc Chabot, Lowell, MA (US)

(73) Assignee: Diagnosys LLC, Lowell, MA (US)

( * ) Notice: Subject to any disclaimer, the term of this patent is extended or adjusted under 35 U.S.C. 154(b) by 691 days.

(21) Appl. No.: 15/348,704

(22) Filed: Nov. 10, 2016

(65) Prior Publication Data

US 2017/0127970 A1 May 11, 2017

Related U.S. Application Data

(60) Provisional application No. 62/253,210, filed on Nov. 10, 2015.

(51) Int. Cl.
*A61B 3/00* (2006.01)
*A61B 5/00* (2006.01)
(Continued)

(52) U.S. Cl.
CPC .......... *A61B 5/0496* (2013.01); *A61B 3/0083* (2013.01); *A61B 3/112* (2013.01); *A61B 3/14* (2013.01); *A61B 5/742* (2013.01)

(58) Field of Classification Search
CPC .......... A61B 5/0496; A61B 3/00–185; A61M 2230/14; A61M 2230/16
See application file for complete search history.

(56) References Cited

U.S. PATENT DOCUMENTS 3,012,472 A * 12/1961 Feinberg ................ A61B 3/032
351/243
3,439,157 A 4/1969 Myles
(Continued)

FOREIGN PATENT DOCUMENTS

| CN | 101019760 | 8/2007 |
|---|---|---|
| EP | 0 225 072 | 6/1987 |

(Continued)

OTHER PUBLICATIONS

Burr-Brown Products From Texas Instruments, Single-Supply Differential Amplifier, Texas Instruments Incorporated, Jan. 2001.
(Continued)

*Primary Examiner* — Patrick Fernandes
(74) *Attorney, Agent, or Firm* — Pandiscio & Pandiscio

(57) ABSTRACT

Apparatus for the assessment of electrophysiological signals obtained from a patient, the apparatus comprising: a housing; a support arch pivotally mounted to the housing, the support arch comprising a plurality of facial contact point supports for supporting contact points on the face of the patient relative to the support arch without supporting the chin of the patient; at least one display screen for presenting a stimulus to a single eye of the patient, the at least one display screen being movable relative to the support arch; and control electronics disposed within the housing for driving the at least one display screen and for amplifying electrophysiological signals obtained from the patient.

24 Claims, 7 Drawing Sheets

(51) Int. Cl.
*A61B 5/0496* (2006.01)
*A61B 3/14* (2006.01)
*A61B 3/11* (2006.01)

(56) References Cited

U.S. PATENT DOCUMENTS

| | | | |
|---|---|---|---|
| 4,131,113 A | 12/1978 | Fender et al. | |
| 4,362,164 A * | 12/1982 | Little | A61B 5/0404 |
| | | | 600/382 |
| 4,618,230 A | 10/1986 | Ens et al. | |
| 4,740,072 A * | 4/1988 | Griffin | A61B 3/024 |
| | | | 351/239 |
| 4,806,289 A | 2/1989 | Laursen et al. | |
| 4,874,237 A | 10/1989 | Cringle | |
| 4,910,090 A | 3/1990 | Kuhlman et al. | |
| 5,141,305 A * | 8/1992 | Young | A61B 3/112 |
| | | | 351/210 |
| 5,943,110 A | 8/1999 | Zeimer | |
| 6,231,187 B1 | 5/2001 | Munoz et al. | |
| 8,810,482 B2 | 8/2014 | Abdollahi et al. | |
| 2003/0020875 A1 | 1/2003 | Sperling | |
| 2003/0149350 A1* | 8/2003 | Porciatti | A61B 3/12 |
| | | | 600/399 |
| 2006/0058857 A1 | 3/2006 | Tano et al. | |
| 2006/0244915 A1* | 11/2006 | Clemons | A61B 3/032 |
| | | | 351/245 |
| 2008/0294066 A1* | 11/2008 | Hetling | A61B 5/0496 |
| | | | 600/558 |
| 2010/0091242 A1* | 4/2010 | Baglini | A61B 5/7228 |
| | | | 351/205 |
| 2010/0249532 A1* | 9/2010 | Maddess | A61B 5/04842 |
| | | | 600/300 |
| 2010/0292999 A1 | 11/2010 | Verma | |
| 2011/0170064 A1* | 7/2011 | Taylor | A61B 3/0083 |
| | | | 351/209 |
| 2012/0069296 A1* | 3/2012 | Li | A61B 3/08 |
| | | | 351/201 |
| 2013/0242077 A1 | 9/2013 | Lin et al. | |
| 2013/0278899 A1 | 10/2013 | Waldorf et al. | |
| 2013/0285886 A1 | 10/2013 | Pombo et al. | |
| 2014/0128763 A1 | 5/2014 | Fadem | |
| 2015/0029463 A1 | 1/2015 | Hetling et al. | |
| 2015/0313467 A1 | 11/2015 | Sakai et al. | |
| 2017/0014074 A1 | 1/2017 | Etzkorn et al. | |
| 2017/0042441 A1 | 2/2017 | Doran et al. | |

FOREIGN PATENT DOCUMENTS

| | | |
|---|---|---|
| EP | 2314201 | 4/2011 |
| WO | WO 2015/191240 | 12/2015 |
| WO | WO 2016/162796 | 10/2016 |

OTHER PUBLICATIONS

Heath, Janet, Amplifiers: What do rail-to-rail and single supply mean?, Analog IC Tips, Oct. 10, 2017.

Lug, Xunda et al., Retinal Pathway Origins of the Pattern Electroretinoaram (PERG), investigative Ophthalmology & Visual Science, vol. 32, No. 12, Nov. 2011, pp. 8571-8584.

Matsumo Celso S. et al., Pattern Visual Evoked Potentials Elicited by Organic Electroluminescence Screen, BioMed Research international, Aug. 14, 2014, pp. 1-6.

Viswanathan, Suresh et al., The Uniform Field and Pattern ERG in Macaques with Experimental Glaucoma: Removal of Spiking Activity, Investigative Ophthalmology & Visual Science, vol. 41. No. 9, Aug. 2000, pp. 2797-2810.

* cited by examiner

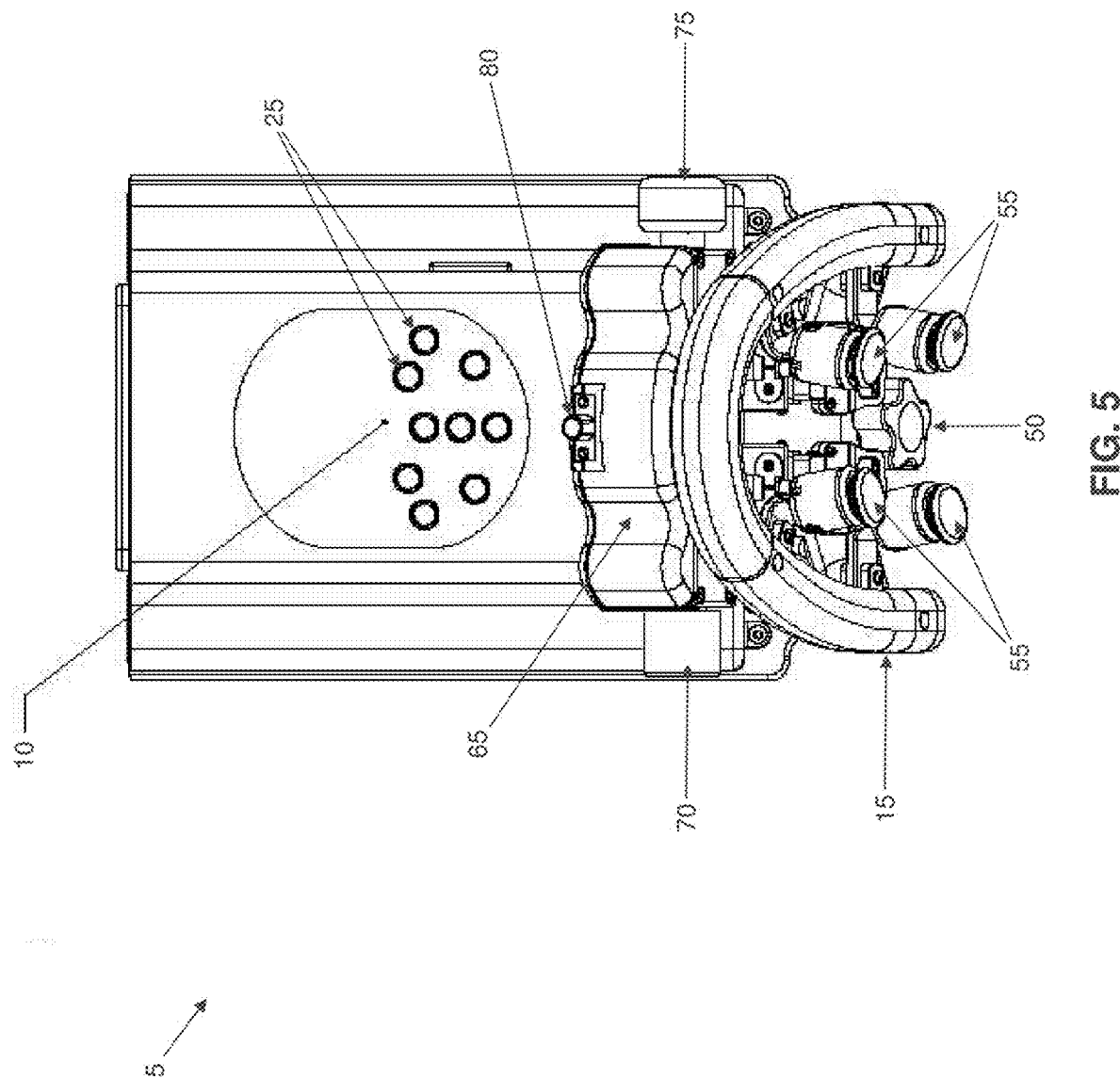

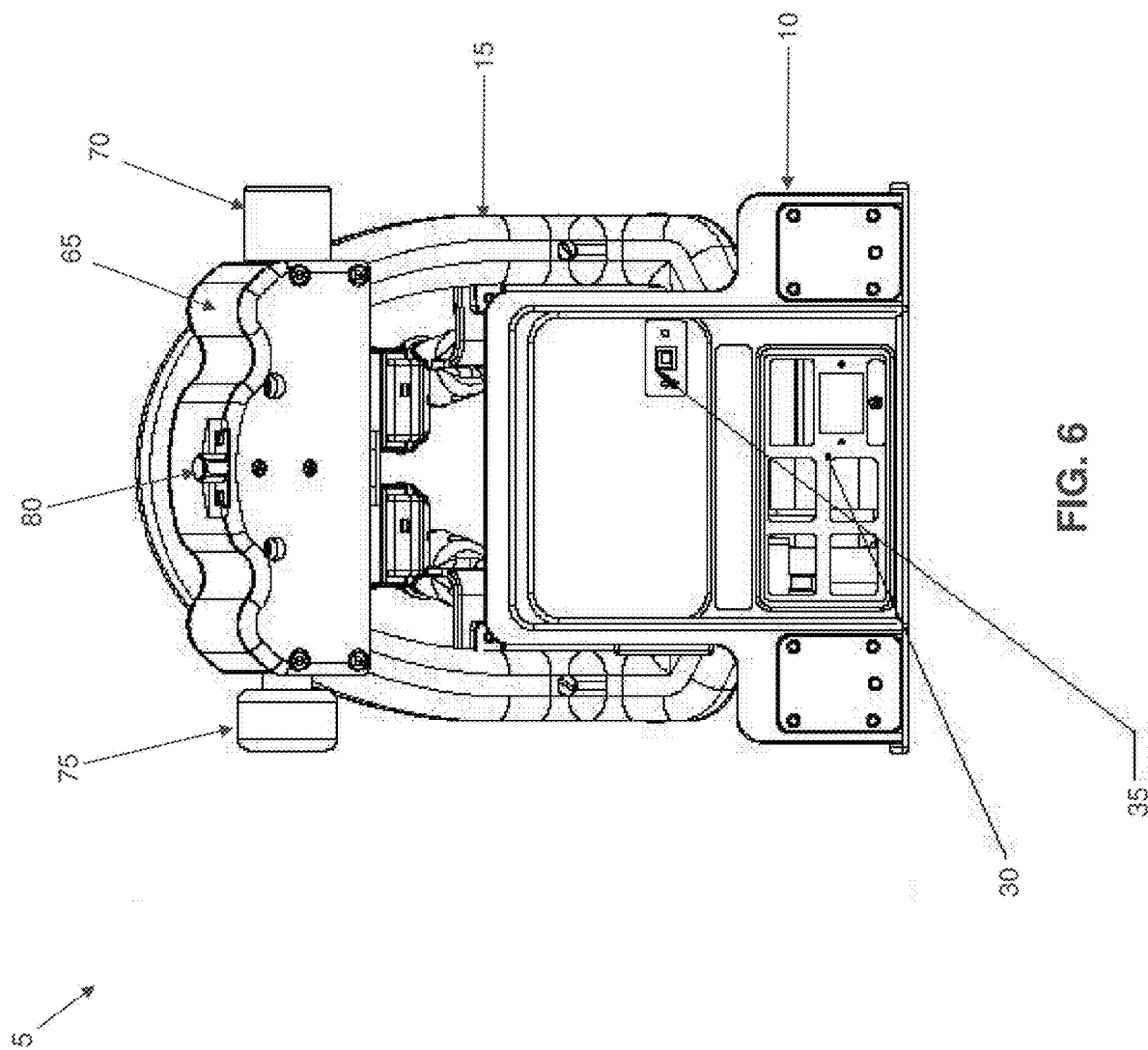

METHOD AND APPARATUS FOR THE ASSESSMENT OF ELECTROPHYSIOLOGICAL SIGNALS

REFERENCE TO PENDING PRIOR PATENT APPLICATION

This patent application claims benefit of prior U.S. Provisional Patent Application Ser. No. 62/253,210, filed Nov. 10, 2015 by Diagnosys LLC and Bruce Doran et al. for METHOD AND APPARATUS FOR THE ASSESSMENT OF ELECTROPHYSIOLOGICAL SIGNALS, which patent application is hereby incorporated herein by reference.

FIELD OF THE INVENTION

This invention relates to apparatus and methods for the assessment of electrophysiological signals in general, and more particularly to apparatus and methods for the assessment of ophthalmic electrophysiological signals.

BACKGROUND OF THE INVENTION

Ophthalmic electrophysiology involves stimulating the eye with light and measuring the resultant electrical responses either from the retina or the visual cortex.

The stimulating light may either consist of homogenous light delivered to the entire retina by a Ganzfeld stimulator (i.e., a full-field stimulator), or a spot or pattern of light usually delivered by a so-called "free-viewing screen" such as a computer monitor.

In order to monitor the patient's electrical response to either type of photic stimulation, electrodes (sometimes inappropriately called sensors) must be applied to the patient.

Electroretinograms

When it is desired to measure the electrical response from the retina, a so-called "active" electrode must be applied to the cornea or to the skin beneath the eye. This electrode conducts the small voltage that appears at the cornea (or the skin beneath the eye) in response to light stimulation to one input of a differential amplifier, the other input of which is connected to a "reference" or "indifferent" electrode usually placed on the skin near the temporal canthus of the same eye. Usually, a third electrode, called a "ground", is placed elsewhere on the skin of the patient (e.g., on the forehead, ear, wrist, etc.). This electrode defines the average common mode voltage of the amplifier and also serves to reduce line noise. Recordings of electrical activity obtained from the retina in response to photic stimulation are called electroretinograms (ERGs).

Visual Evoked Potentials

When it is desired to measure the electrical response from the brain (usually the visual cortex), skin electrodes are placed on the scalp. Generally, one or more electrodes are placed over the visual cortex near the inion on the back of the head, with a reference at the forehead and a ground on the top of the head or on the ear lobes, but other arrangements are also possible. Recordings of electrical activity obtained in response to photic stimulation from the brain are called visual evoked potentials (VEPs).

Clinical Challenges

A number of clinical challenges are encountered in recording ERGs and VEPs.

1. One problem associated with performing pattern electroretinography (PERG) or pattern visual evoked potentials (PVEP) is positioning the patient in front of a pattern display so that the patient's eyes are correctly aligned with, and at the proper distance from, the display. An adjustable chin support is usually used to position and stabilize the head of the patient. Patients rest their chins on the chin support, and the chin support is raised or lowered as necessary to adjust the head height of seated patients so that their eyes align with the display. Chin rests can be uncomfortable because they can bend the neck at an awkward angle. Electrophysiology testing can last several minutes and typically require patients to sit longer than is required for tests that traditionally use chin rests, such as optical coherence tomography (OCT) or fundus photography. Uncomfortable patients are less inclined to tolerate longer procedures and, even when co-operative, tend to produce poor recordings because the patients fidget. Moreover, patients often self-correct minor misalignment by tightening their jaws. This is undesirable because electrical signals from the facial musculature can interfere with the electroretinography (ERG) signals, which in the case of PERG are extremely small. In addition to these disadvantages, chin rests provide only approximate positioning, even when combined with a forehead rest. Therefore, it would be desirable to support the head of the patient in front of the display without requiring the use of a chin support, both to enhance patient comfort and to improve accurate and stable positioning of the eyes relative to the stimulus.

2. The display used for performing pattern ophthalmic electrophysiology is typically a cathode ray tube (CRT). The CRT is a good choice for some types of tests, such as PERG, because it produces no luminance artifact (i.e., there is no unwanted change in the mean luminance when a checkerboard or grating displayed on the screen changes handedness). However, CRT screens are an obsolete technology and have become difficult to source, and in any case have historically been too dim to generate an optimal signal-to-noise ratio in PERG and Multifocal ERG tests. This limits the utility of CRT screens for performing these tests. Therefore, it would be desirable to provide currently-manufactured displays with brighter screens and no luminance artifact to provide ready availability as well as greater reproducibility in performing these tests.

3. Because existing pattern displays are large, no existing pattern ophthalmic electrophysiology stimulator is provided as a pair, i.e., with one display for each eye. If it is desired to stimulate only one eye (e.g., pattern VEP), the fellow eye must be patched. This procedure is cumbersome but accomplishes the desired purpose. However, some tests that would be desirable to perform require presenting a modulated pattern to one eye while simultaneously presenting a differently modulated pattern to the other eye (the difference could be in temporal or spatial modulation, or both). This cannot be properly accomplished using a single display (a 3D display could theoretically be used, but in general would not be practical because of poor luminance control, unacceptably large crosstalk between the two eyes, difficulty with mechanical interference with electrodes, and uncontrollable luminance artifact). Therefore, it would be desirable to provide a pattern ophthalmic electrophysiology stimulator which comprises one display for each eye.

4. Pattern electrophysiology must be conducted in an undilated eye in order to preserve image quality on the retina. Thus the amplitude of the pattern ERG can be variable because the amount of light reaching the retina depends on the dilation of the patient's pupil, which is uncontrolled. While it is possible to measure the dilation of the pupil and adjust the stimulator luminance appropriately, this method has the drawback that effective retinal illuminance depends on more than just pupil diameter (note the Stiles-Crawford effect, etc.). Therefore, it would be desirable to provide a novel method for controlling the dilation of the pupil in an unmedicated eye.

5. In present configurations for performing ophthalmic electrophysiology on human patients, at least three electrodes are typically attached to the patient: (i) a ground electrode (applied to the skin); (ii) a reference electrode; and (iii) a corneal (active) electrode. The electrode which is used as the ground electrode is easy to attach to the patient because its position is not critical—anywhere on the body of the patient will suffice. Placement of the other two electrodes (i.e., the reference electrode and the active electrode) requires more care. The reference electrode must be placed in the proper location on the patient, usually on the skin at the temporal canthus. Mispositioning of the reference electrode can cause imbalances in the readings that are obtained. In addition, the fact that the corneal electrode enjoys a saline tear bridge to body tissue, and the skin electrode (i.e., the reference electrode) is connected to body tissue through the epithelium, introduces another imbalance. If both eyes of the patient are to be tested, a second corneal electrode must be placed in the fellow eye in a homologous position to the first. An existing device (i.e., a "DTL thread electrode") is commonly used as the active electrode for human patients. More particularly, a DTL thread electrode comprises a seven-stranded fiber which is suspended across the eye such that the electrode makes electrical contact with the cornea, with the electrode secured in the corners of the eye using two pads. Typically, the DTL thread electrode is used in combination with a reference electrode placed on the temple of the patient. One of the most significant clinical challenges associated with performing ophthalmic electrophysiology is properly connecting the electrodes to the patient and, more particularly, properly connecting the reference electrode to the patient so as to yield an accurate electroretinography (ERG) signal. The electroretinography (ERG) signal can vary significantly depending upon where the reference electrode is placed on the head of the patient (e.g., on the cheek, temple, etc.) and, for this reason, typically requires skilled personnel in order to be correctly placed. Therefore, it would be desirable to eliminate the need for a separate reference electrode in order to avoid errors resulting from mispositioning of the reference electrode.

6. In addition, the electrical connections between the corneal, reference, and ground electrodes and the physiological amplifier take the form of a lead wire or wires running from the electrodes to input connections on the amplifier. In most current configurations, the amplifier is located behind or to one side of the patient. In these configurations, the amplifier wires can run over electrically uncontrolled surfaces, such as an ungrounded metal table, and may also become separated from each other in such a way as to form an unintended antenna. When so arranged, the lead wires can pick up electrical noise whose origin may not be clear to an inexperienced user. Therefore, it would be desirable to locate the amplifier in a position that would automatically ensure correct routing of the patient leads so as to minimize electrical issues.

7. All pattern displays in current use are large, free-viewing monitors. These monitors generally use either obsolete CRT technology, or are LCD-based. LCD monitors universally produce a large luminance artifact and have been specifically deemed inappropriate for pattern ERG and pattern VEP by the International Society for the Electrophysiology of Vision. The only exception to this are highly specialized Maxwellian view projection displays that can only stimulate a single eye. These specialized Maxwellian displays require unusual expertise on the part of the clinician and take considerable time to properly set up, rendering them generally unsuitable for clinical use. Moreover, Maxwellian view displays that stimulate both eyes simultaneously do not exist. Free-viewing OLED monitors exist, but most are temporally modulated at 60 Hz, which renders them unsuitable as electrophysiology stimulators, and the few that are not temporally modulated at 60 Hz are even dimmer than CRT displays and hence inadequate as electrophysiology stimulators. Therefore, it would be desirable to provide a small, high-brightness display capable of presenting a high-luminance stimulus that is free of luminance artifact, while at the same time being small enough to present a stimulus to both eyes simultaneously.

Thus there is a need for a new and improved method and apparatus which:

(i) supports the head of a patient relative to the display used to perform electroretinography (ERG) while eliminating the need for a chin rest;

(ii) provides an improved display for performing electroretinography (ERG) that is obtainable (i.e., currently manufactured), brighter than a CRT, and has no luminance artifact so as to allow a greater range of diagnostic tests;

(iii) provides a means of simultaneously stimulating each eye with patterns that are different, either temporally or spatially, or both (e.g., by displaying a different, dichoptic pattern to each eye);

(iv) provides a means of stimulating one eye with a modulated pattern, while illuminating the other, reference eye with a steady light in order to control the size of undilated pupils (e.g., to control pupil dilation nonmydriatically by presenting a steady background, either controlled by pupillometry feedback or open loop, to the unstimulated eye);

(v) eliminates the need for separate reference electrodes for each of the two active electrodes used in electroretinography (ERG);

(vi) locates the amplifier in a position that automatically ensures correct routing of the electrode lead wires; and (vii) comprises a unit more compact than is possible with the free-viewing pattern displays currently in use (e.g., by providing dual eye stimulation in a single, self-contained unit that is considerably smaller than any existing technology with similar capabilities).

SUMMARY OF THE INVENTION

The present invention addresses these and other objects by the provision and use of a novel method and apparatus for the assessment of electrophysiological signals.

In one form of the invention, there is provided apparatus for the assessment of electrophysiological signals obtained from a patient, the apparatus comprising:

a housing;

a support arch pivotally mounted to the housing, the support arch comprising a plurality of facial contact point supports for supporting contact points on the face of the patient relative to the support arch without supporting the chin of the patient;

at least one display screen for presenting a stimulus to a single eye of the patient, the at least one display screen being movable relative to the support arch; and control electronics disposed within the housing for driving the at least one display screen and for amplifying electrophysiological signals obtained from the patient.

In another form of the invention, there is provided a method for the assessment of electrophysiological signals obtained from a patient, the method comprising:

providing apparatus comprising:
a housing;
a support arch pivotally mounted to the housing, the support arch comprising a plurality of facial contact point supports for supporting contact points on the face of the patient relative to the support arch without supporting the chin of the patient;
at least one display screen for presenting a stimulus to a single eye of the patient, the at least one display screen being movable relative to the support arch; and
control electronics disposed within the housing for driving the at least one display screen and for amplifying electrophysiological signals obtained from the patient;

positioning the patient relative to the housing;

adjusting the support arch relative to the housing so as to properly support the face of the patient relative to the housing, and adjusting the at least one display screen relative to the support arch; and stimulating an eye of the patient with the at least one display screen and obtaining an electrophysiological signal from the patient.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 5 is a schematic top view of the novel electroretinography (ERG) apparatus of FIG. 1;

FIG. 6 is a schematic rear view of the novel electroretinography (ERG) apparatus of FIG. 1.

DETAILED DESCRIPTION OF THE PREFERRED EMBODIMENTS

Figure 1:
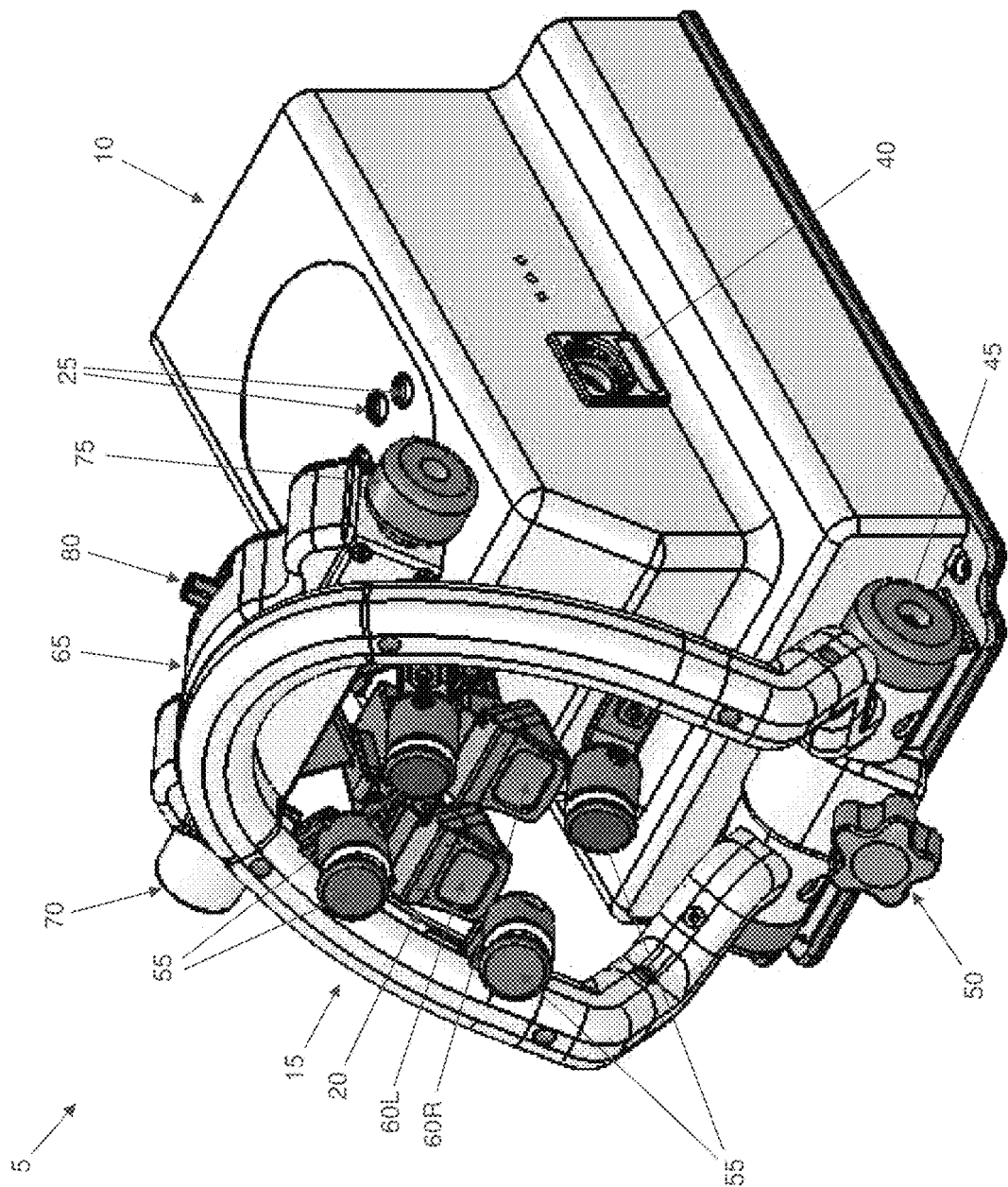
FIG. 1 is a schematic perspective view of a novel electroretinography (ERG) apparatus formed in accordance with the present invention.
Figure 2:
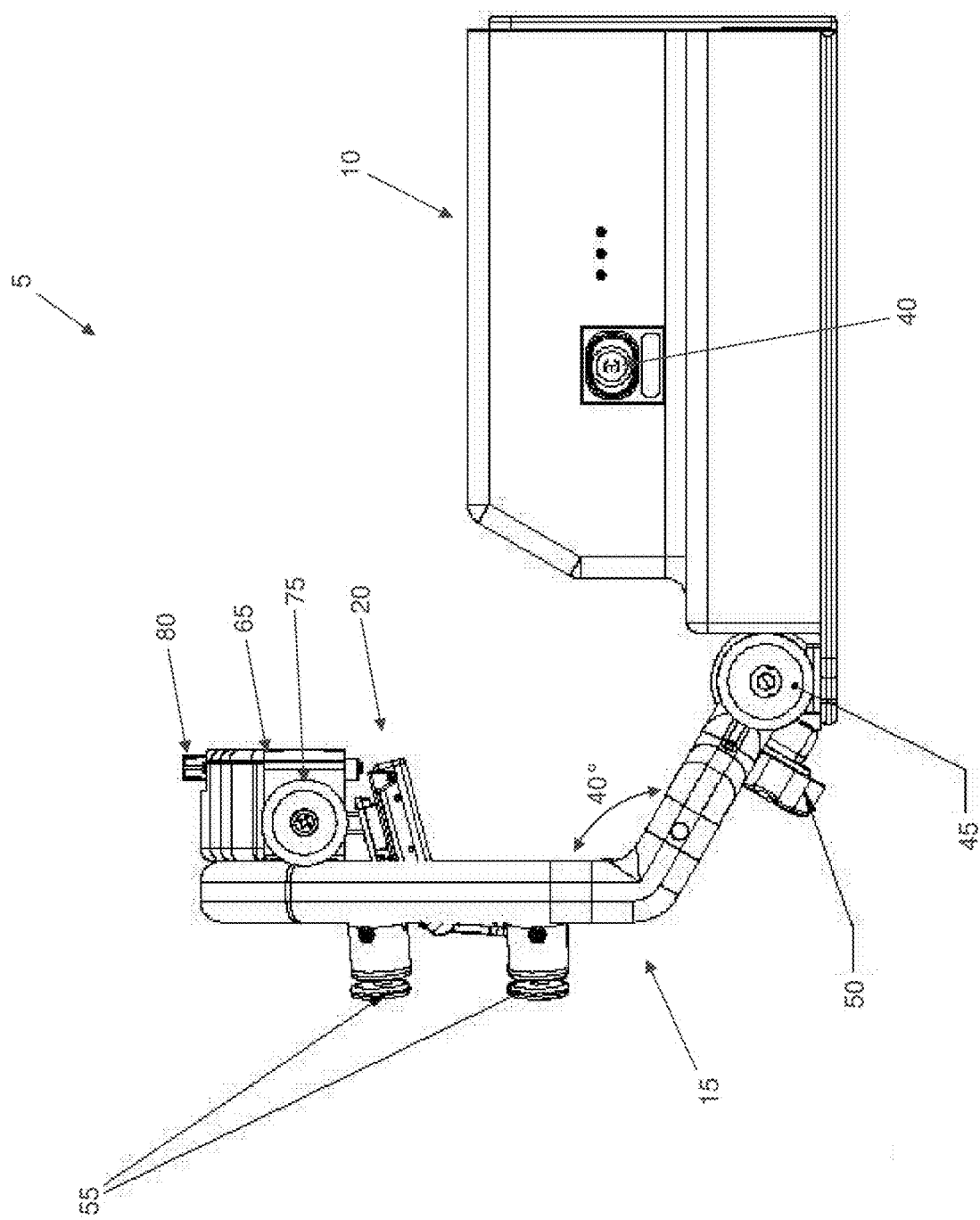
FIGS. 2 and 3 are schematic side views of the novel electroretinography (ERG) apparatus of FIG. 1.
Figure 3:
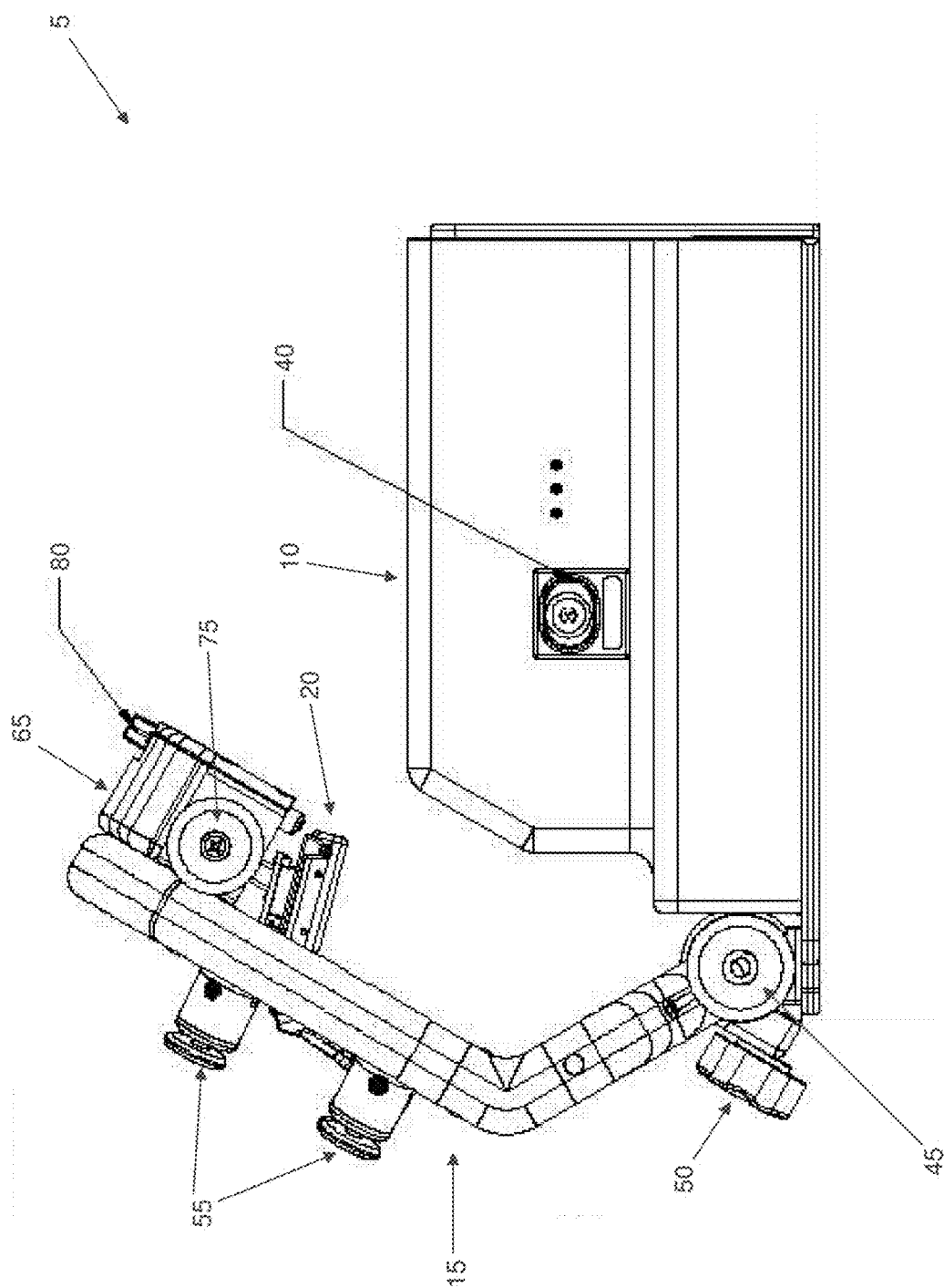
Figure 4:
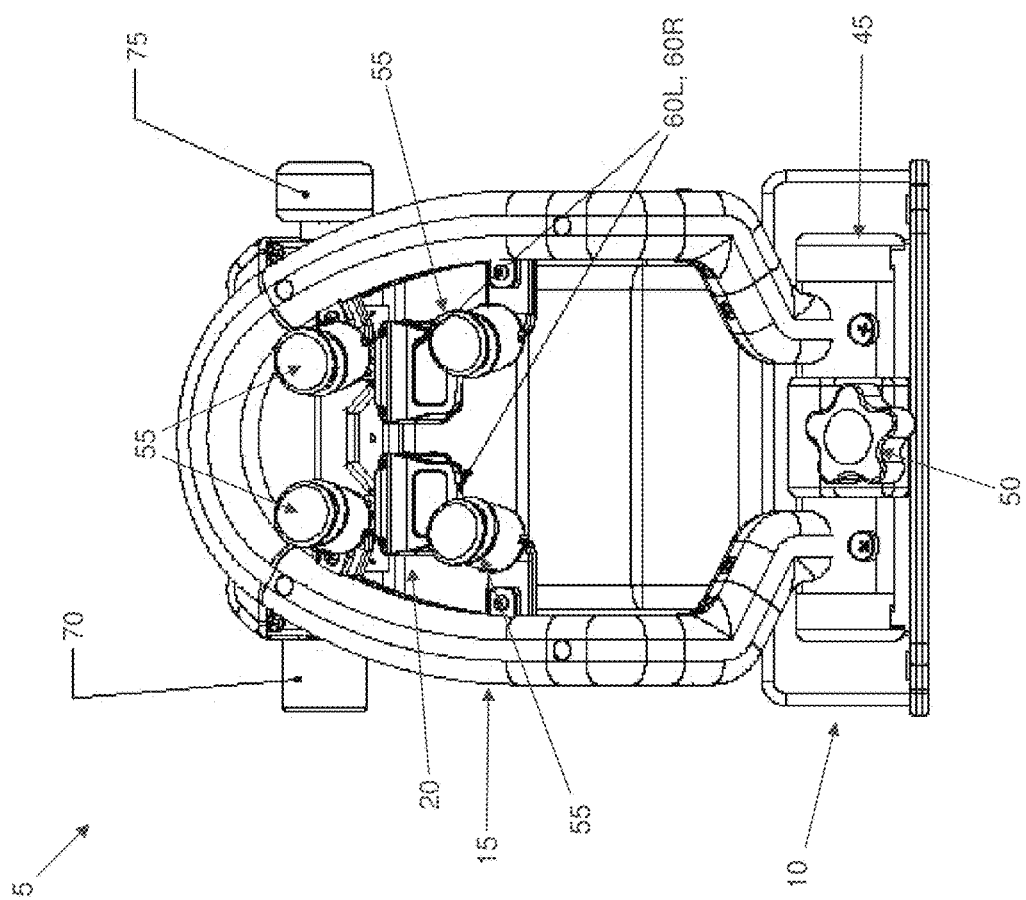
FIG. 4 is a schematic front view of the novel electroretinography (ERG) apparatus of FIG. 1.

As will hereinafter be discussed, the present invention provides a new and improved method and apparatus which:

(i) supports the head of a patient relative to the display used to perform electroretinography (ERG) while eliminating the need for a chin rest;

(ii) provides an improved display for performing electroretinography (ERG) that is obtainable (i.e., currently manufactured), brighter than a CRT and has no luminance artifact so as to allow a greater range of diagnostic tests;

(iii) provides a means of simultaneously stimulating each eye with patterns that are different, either temporally or spatially, or both (e.g., by displaying a different, dichoptic pattern to each eye);

(iv) provides a means of stimulating one eye with a modulated pattern, while illuminating the other, reference eye with a steady light in order to control the size of undilated pupils (e.g., to control pupil dilation nonmydriatically by presenting a steady background, either controlled by pupillometry feedback or open loop, to the unstimulated eye);

(v) eliminates the need for separate reference electrodes for each of the two active electrodes used in electroretinography (ERG);

(vi) locates the amplifier in a position that automatically ensures correct routing of the electrode lead wires; and (vii) comprises a unit more compact than is possible with the free-viewing displays currently in use (e.g., by providing dual eye stimulation in a single, self-contained unit that is considerably smaller than any existing technology with similar capabilities).

More particularly, and looking now at FIGS. 1-6, there is shown a novel electroretinography (ERG) apparatus 5 formed in accordance with the present invention. Electroretinography (ERG) apparatus 5 generally comprises a control enclosure (or housing) 10, a support arch 15, and a display 20.

Control enclosure 10 is configured to be mounted to, or set on top of, a table (not shown) such that control enclosure 10 is disposed approximately at eye level with a patient seated in front of the control enclosure. Control enclosure 10 comprises control electronics for (i) driving display 20, and (ii) processing anatomical electrical signals evoked by display 20, e.g., a physiological amplifier (not shown), a plurality of physiological amplifier input ports 25 formed in the top surface of control enclosure 10 for connecting the corneal, reference and ground electrodes (not shown) to the physiological amplifier, etc.

Control enclosure 10 also comprises a power panel 30 (FIG. 6) for providing electrical power to the control electronics contained in control enclosure 10 (and/or for providing electrical power to an external computer and/or other accessories connected to control enclosure 10) and a USB connection 35 (FIG. 6) for controlling/programming (i) the control electronics contained in control enclosure 10, and/or (ii) display 20, e.g., via an external computer (not shown).

If desired, control enclosure 10 may also comprise a Ganzfeld connection 40 (FIG. 1) for connecting a Ganzfeld bar accessory (not shown) which may be mounted to support arch 15 and used to perform full field electroretinography (ERG). Support arch 15 is pivotally mounted to control enclosure 10 (e.g., at the base of control enclosure 10) by way of a pivot bearing 45 (sometimes hereinafter referred to as a "rotational pivot"). A locking control knob 50 (e.g., a threaded screw and knob) is provided at the base of pivot bearing 45 for releasably securing support arch 15 against rotation around pivot bearing 45 (i.e., to secure support arch 15 in position after support arch 15 has been rotated about pivot bearing 45 to a desired position). In one preferred form of the invention, support arch 15 is bent at an angle of approximately 40 degrees (FIG. 2) proximate to where support arch 15 is mounted to pivot bearing 45, whereby to facilitate alignment of support arch 15 (and hence display 20) with the head of a patient, as will hereinafter be discussed in greater detail.

A plurality of patient supports 55 (FIG. 1) are mounted to support arch 15 for contacting the face of a patient (i.e., the plurality of patient supports 55 collectively define a "facial resting area") as will hereinafter be discussed. In one preferred form of the invention, patient supports 55 are configured so that two of the patient supports 55 engage the forehead of the patient and two of the patient supports 55 engage the cheeks of the patient. Note that patient supports 55 make "point contacts" with the face of the patient (as opposed to large, extended surface area contacts with the face of the patient, such as might be provided by a face mask, or by an extended support bar, etc.) and do not engage the underside of the chin of the patient. In one preferred form of the invention, each patient support 55 has a surface area of approximately 2-6 square centimeters. Patient supports 55 are preferably either spring-mounted to, or fixed with relation to, support arch 15, and may be independently adjustable relative to support arch 15 so as to accommodate the anatomical differences of a wide range of patients. Patient supports 55 may be cushioned or uncushioned. In a preferred form of the present invention, four patient supports 55 are provided, however, it should be appreciated that a greater or lesser number of patient supports 55 may be provided if desired.

If desired, patient supports 55 may be configured to also be used as electrodes, eliminating the need for separate application of one or more types of electrodes. By way of example but not limitation, patient supports 55 may provide a conductive element configured to contact the skin of a patient when the face of a patient is supported on patient supports 55. By way of further example but not limitation, patient supports 55 may be configured to be used as ground electrodes when the face of a patient is supported on patient supports 55.

Display 20 comprises a pair of independently movable screens 60L, 60R (sometimes hereinafter referred to as "pattern displays") which are mounted to the upper portion of support arch 15 by way of a display mount 65 (FIG. 1). In one preferred form of the present invention, independently movable screens 60L, 60R comprise organic light-emitting diode (OLED) screens for independently (i.e., dichoptically) delivering an image to the left eye and/or the right eye of a patient, respectively. Significantly, the OLED screens used to form screens 60L, 60R are not modulated except by the pattern displayed thereon and are free of luminance artifact, so they are highly suitable as electrophysiology stimulators. It is believed that providing screens 60L, 60R, formed out of OLEDs which are not modulated except by the pattern thereon, provides a novel electrophysiology stimulator.

In one preferred form of the invention, each of the screens 60L, 60R has at least one optical element disposed in front thereof, so that magnified images of the screens 60L, 60R are presented to the eyes of the user.

Display mount 65 comprises a rotational control knob 70 for selectively pivoting display 20 (and hence, independently movable screens 60L, 60R) toward and away from the plane defined by support arch 15 (i.e., toward and away from the face of a patient supported on patient supports 55). Note that independently movable screens 60L, 60R may be mounted to display mount 65 so that independently movable screens 60L, 60R are coplanar with one another, or so that independently movable screens 60L, 60R are held at a fixed angle relative to one another, or so that independently movable screens 60L, 60R are held at a variable angle relative to one another. Display mount 65 also comprises an inner ocular control knob 75 for selectively moving independently movable screens 60L, 60R either toward one another or away from one another, whereby to accommodate different ocular distances between the left and right eyes (as can vary among different patients). Display mount 65 also comprises a height control knob 80 for selectively moving independently movable screens 60L, 60R up or down relative to support arch 15 (i.e., up or down relative to the face of a patient supported on patient supports 55).

Thus it will be seen that support arch 15 is adjustably mounted to control enclosure (or housing) 10 via pivot bearing 45; display mount 65 is mounted to support arch 15; display 20 is adjustably mounted to display mount 65, with position adjustments being made by rotational control knob 70 and height control knob 80; and independently movable screens 60L, 60R are adjustably mounted to display 20, with positional adjustments being made by inner ocular control knob 75 for selectively moving independently movable screens 60L, 60R either toward one another or away from one another, and with independently movable screens 60L, 60R being capable of variable positioning with respect to display 20, e.g., so that independently movable screens 60L, 60R may be adjustably positioned relative to the eyes of the patient and to one another.

It will be appreciated that a patient can be seated in front of electroretinography (ERG) apparatus 5 and support arch 15 can be pivoted about pivot bearing 45 so as to align patient supports 55 with the face of the patient. Support arch 15 is then secured in place against rotation about pivot bearing 45 by tightening control knob 50.

The patient then rests their face on patient supports 55, and the position of independently movable screens 60L, 60R is adjusted by way of rotational control knob 70, inner ocular control knob 75 and height control knob 80 so as to properly align independently movable screens 60L, 60R with the left and right eyes of the patient, respectively. By virtue of this construction, it will be appreciated that a chin support is not required, and the patient may rest their face on patient supports 55 without tightening the facial musculature, thereby facilitating a superior diagnostic result. Furthermore, inasmuch as support arch 15 is bent near its base at an angle of approximately 40 degrees (see FIG. 2), it will be appreciated that support arch 15 can accommodate a wide range of different patient heights without requiring that the entire electroretinography (ERG) apparatus 5 be moved up or down relative to the patient. More particularly, in order to accommodate a relatively tall patient, support arch 15 is pivoted about pivot bearing 45 towards control enclosure 10 such that the patient is "looking down" into independently movable screens 60L, 60R; in order to accommodate a relatively short patient, support arch 15 is pivoted about pivot bearing 45 away from control enclosure 10 such that the patient is "looking up" into independently movable screens 60L, 60R.

It will also be appreciated that since display 20 is mounted to support arch 15 (i.e., via display mount 65), and since support arch 15 is directly pivotally mounted to control enclosure 10, the distance between the electrodes (mounted to the patient) and physiological amplifier input ports 25 is greatly reduced over prior art amplifier/display systems, and that lead wires running from the electrodes (mounted to the patient) to the amplifier input ports 25 are led over the main body of the control enclosure 10 which forms a controlled scheme to minimize differential capacitive coupling between the various lead wires and EMI sources in the room. One or more cables (not shown) extend from the patient electrodes, along the top of control enclosure 10, e.g., in grooves (not shown) formed on the top surface of control enclosure 10, and into the plurality of physiological amplifier input ports 25 formed in the top surface of control enclosure 10, so as to electrically connect the patient electrodes to the physiological amplifier inputs 25 (and hence to the control electronics contained within control enclosure 10). By virtue of this construction, the cables connecting the patient to the physiological amplifier inputs 25 (and hence to the control electronics contained within control enclosure 10) do not run adjacent to any electrically uncontrolled surfaces (e.g., an ungrounded metal table top), and therefore are not subject to electromagnetic interference which may otherwise degrade the signal sent from the patient electrodes to physiological amplifier inputs 25 (and hence to the control electronics contained within control enclosure 10).

Additionally, since independently movable screens 60L, 60R are independently drivable, it is possible to stimulate each of the eyes independently of one another in a dichoptic fashion. By way of example but not limitation, by utilizing a pair of DTL thread electrodes (i.e., one electrode contacting the cornea of the left eye and one electrode contacting the cornea of the right eye), it will be appreciated that when the left eye is stimulated (i.e., by screen 60L), the DTL thread electrode contacting the right eye can act as the reference electrode. And it will be appreciated that when the right eye is stimulated (i.e., by screen 60R), the DTL thread electrode contacting the left eye can act as the reference electrode. Hence, with an electrode configuration that utilizes two DTL thread electrodes, the need for a separate reference electrode attached to the head of a patient is eliminated. Thus, possible errors introduced by misplacement of the reference electrode are also eliminated. This is a significant advance in the art.

Also, a steady background light produced by the display (e.g., screen 60L or 60R) driving the unstimulated eye can be used to force the pupil of the stimulated eye to a particular diameter, with the process being controlled by either (i) utilizing a pupillometry camera or cameras, focused on each eye, to regulate the intensity of the steady background light, or (ii) by simply driving the background light to a known luminance. This approach is possible because, anatomically, when the pupil in one eye is driven to a particular diameter (e.g., by appropriate exposure of light), the pupil in the other eye automatically adjusts to a similar diameter in concert with the driven pupil. In other words, in accordance with the present invention, where one eye is being stimulated for the assessment of electrophysiological signals, and where it is desirable for the stimulated eye to have a known, constant dilation, the unstimulated eye can be presented with an background steady background light that can drive the unstimulated eye to a known, constant dilation, which will in turn cause the stimulated eye to dilate to a known, constant dilation. The dilation of the unstimulated eye can be controlled by a pupillometry camera observing either eye, or by driving the background light to a known luminance. Thus pupil size, and therefore retinal illuminance, can be held constant without dilating the pupil of the eye which is being stimulated for electrophysiological assessment. This approach for controlling pupil diameter is superior to adjusting the stimulation intensity in accordance with a measured diameter of the pupil because retinal illuminance depends on more than just pupil diameter, as explained above. This unique feature is also an important advance in the art.

Figure 8:
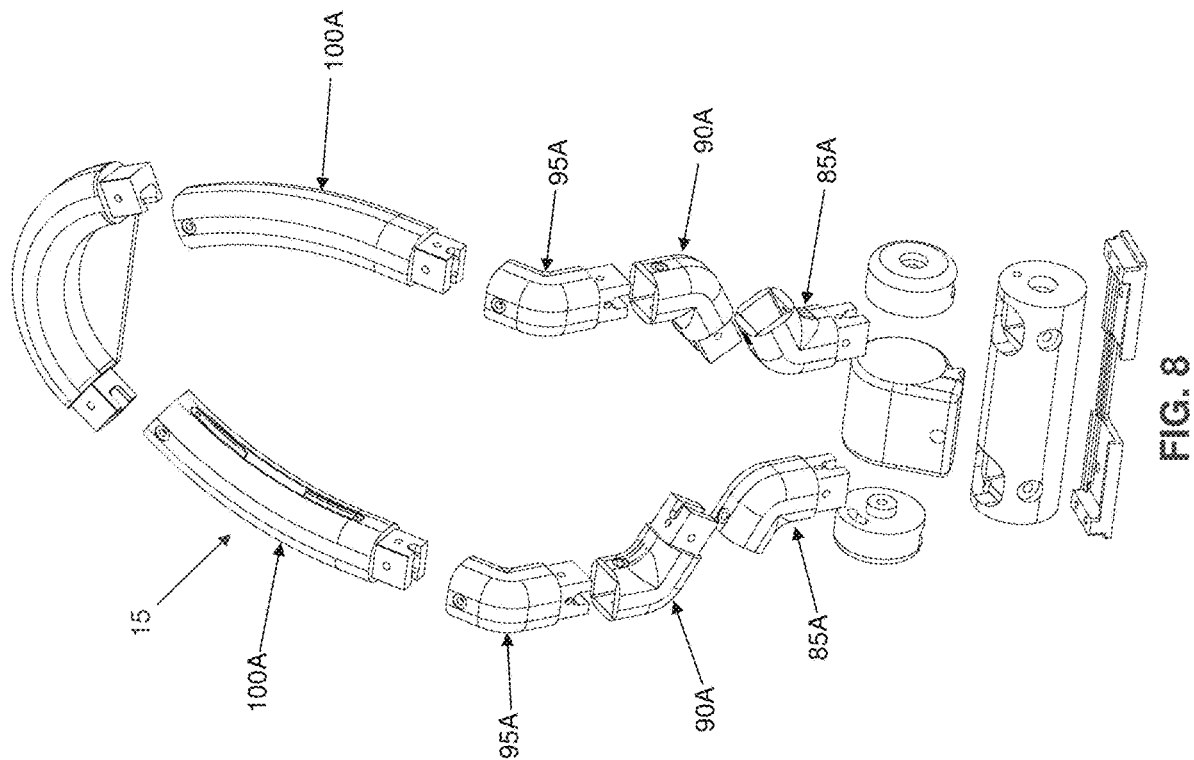
FIGS. 7 and 8 are schematic views showing details of a support arch for the novel electroretinography (ERG) apparatus of FIG. 1.
Figure 7:
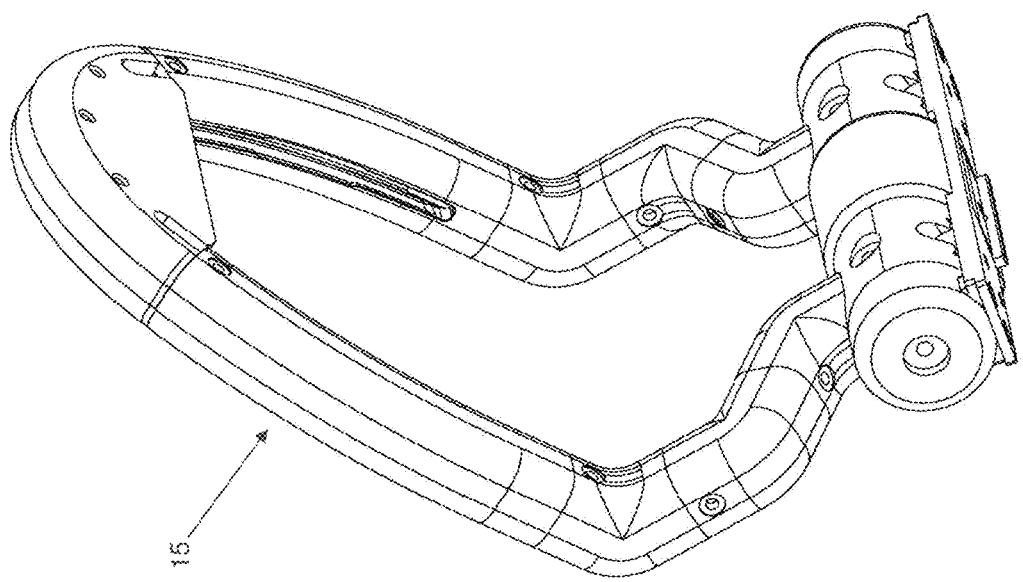

It should also be appreciated that, if desired, support arch 15 may comprise a plurality of "mirrored" sections (i.e., a plurality of "mirror-image" sections 85A, 85B; 90A, 90B; 95A, 95B; 100A, 100B) which are assembled together to make the support arch (see FIGS. 7 and 8). Constructing support arch 15 out of a plurality of "mirrored" segments reduces machining costs and simplifies the manufacture of electroretinography (ERG) apparatus 5.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An apparatus for an assessment of electrophysiological signals obtained from a patient, the apparatus comprising:
a support for supporting a head of the patient;
a first electrode configured to be mounted to a first eye of the patient, and a second electrode configured to be mounted to a second eye of the patient;
a ground electrode configured to be mounted to the patient;
a first display screen disposed before the first eye of the patient for selectively presenting a visual stimulus to the first eye of the patient, and a second display screen disposed before the second eye of the patient for selectively presenting a visual stimulus to the second eye of the patient, the first display screen and the second display screen being movable relative to the support, and the first display screen and the second display screen being configured such that none of the visual stimulus presented to the first eye of the patient by the first display screen is perceived by the second eye of the patient, and none of the visual stimulus presented to the second eye of the patient by the second display screen is perceived by the first eye of the patient; and
control electronics for selectively driving the first display screen and the second display screen, and for amplifying electrophysiological signals obtained from the first electrode and the second electrode; wherein the control electronics are configured to (i) drive the first display screen so as to present a visual stimulus to the first eye of the patient while not driving the second display screen, or to (ii) drive the second display screen so as to present a visual stimulus to the second eye of the patient while not driving the first display screen; and
wherein the control electronics are configured to (i) use the first electrode as an active electrode and to use the second electrode as a reference electrode when the first eye is stimulated by the first display screen, and (ii) use the second electrode as an active electrode and to use the first electrode as a reference electrode when the second eye is stimulated by the second display screen.

2. The apparatus according to claim 1, wherein the support comprises a plurality of contact point supports for supporting a face of the patient, and further wherein the plurality of facial contact point supports are cushioned.

3. The apparatus according to claim 1, wherein the support comprises a plurality of contact point supports for supporting a face of the patient, and further wherein the plurality of facial contact point supports are uncushioned.

4. The apparatus according to claim 1, wherein the support comprises a plurality of contact point supports for supporting a face of the patient, and further wherein at least one of the plurality of facial contact point supports makes an electrical connection with the face of the patient.

5. The apparatus according to claim 4, wherein the at least one of the plurality of facial contact point supports serves as an electrode for the assessment of electrophysiological signals obtained from the patient.

6. The apparatus according to claim 1, wherein the first display screen and the second display screen each comprise a pattern display that does not comprise a luminance artifact.

7. The apparatus according to claim 6, wherein the first display screen and the second display screen each comprise an OLED pattern display.

8. The apparatus according to claim 1, wherein the apparatus further comprises at least one mechanism for adjusting a position of at least one of the first display screen and the second display screen, whereby to permit adjustment of an interocular distance.

9. The apparatus according to claim 1, wherein the control electronics are configured to present a pattern display to the first eye of the patient while presenting no visual stimulus to the second eye of the patient, and further wherein none of the pattern display perceived by the first eye of the patient can be seen by the second eye of the patient.

10. The apparatus according to claim 1, wherein presenting no visual stimulus to the second eye of the patient comprises providing no light to the second eye of the patient or providing a steady light to the second eye of the patient, wherein the steady light may be with or without a pattern.

11. The apparatus according to claim 1, wherein the visual stimulus is a pattern display.

12. The apparatus according to claim 11, wherein the pattern display is temporally and/or spatially modulated.

13. A method for an assessment of electrophysiological signals obtained from a patient, the method comprising:
providing an apparatus comprising:
a support for supporting a head of the patient;
a first electrode configured to be mounted to a first eye of the patient, and a second electrode configured to be mounted to a second eye of the patient;
a ground electrode configured to be mounted to a body of the patient;
a first display screen disposed before the first eye of the patient for selectively presenting a visual stimulus to the first eye of the patient, and a second display screen disposed before the second eye of the patient for selectively presenting a visual stimulus to the second eye of the patient, the first display screen and the second display screen being movable relative to the support, and the first display screen and the second display screen being configured such that none of the visual stimulus presented to the first eye of the patient by the first display screen is perceived by the second eye of the patient, and none of the visual stimulus presented to the second eye of the patient by the second display screen is perceived by the first eye of the patient; and
control electronics for selectively driving the first display screen and the second display screen, and for amplifying electrophysiological signals obtained from the first electrode and the second electrode;
wherein the control electronics are configured to (i) drive the first display screen so as to present a visual stimulus to the first eye of the patient while not driving the second display screen, or to (ii) drive the second display screen so as to present a visual stimulus to the second eye of the patient while not driving the first display screen; and
wherein the control electronics are configured to (i) use the first electrode as an active electrode and to use the second electrode as a reference electrode when the first eye is stimulated by the first display screen, and (ii) use the second electrode as an active electrode and to use the first electrode as a reference electrode when the second eye is stimulated by the second display screen;
adjusting the support so as to properly support the head of the patient, and adjusting the first display screen and the second display screen relative to the support;
mounting the first electrode to the first eye of the patient, mounting the second electrode to the second eye of the patient, and mounting the ground electrode to the body of the patient; and
providing a visual stimulus to one of the first eye of the patient or the second an eye of the patient with the first display screen or the second display screen, respectively, such that (i) if the first eye of the patient is stimulated by the first display screen, an electrophysiological signal is obtained by using the first electrode as the active electrode and the second electrode as the reference electrode, and (ii) if the second eye of the patient is stimulated by the second display screen, an electrophysiological signal is obtained by using the second electrode as the active electrode and the first electrode as the reference electrode.

14. The method according to claim 13, wherein the first eye of the patient and the second eye of the patient are stimulated one at a time so as to produce an ERG response which is traceable to a specific eye of the patient without requiring intervention by a clinician.

15. The method according to claim 13, wherein the first eye of the patient and the second eye of the patient are stimulated one at a time for producing a VEP response traceable to a specific eye of the patient without requiring intervention by a clinician.

16. The method according to claim 13, wherein the control electronics are configured so as to allow a pupil size of an undilated, stimulated eye of the patient to be controlled by presenting a steady background light to an unstimulated eye of the patient in order to contract pupils of both the undialted, stimulated eye and the unstimulated eye to a given size.

17. The method according to claim 16, wherein the luminance of the steady background light is set by the control electronics.

18. The method according to claim 16, wherein pupil size is regulated by either pupillometry feedback or an open loop.

19. The method according to claim 18, wherein pupillometry feedback is obtained from at least one camera mounted near at least one eye of the patient.

20. The method according to claim 13, wherein the apparatus is configured to allow simultaneous recording of both ERG and VEP responses from each of the first eye and the second eye of the patient separately without intervention by a clinician.

21. The method according to claim 13, wherein the control electronics are configured to measure both the electrophysiological signal received from the first eye of the patient and the electrophysiological signal received from the second eye of the patient by permitting both the first electrode and the second electrode to be plugged into a single amplifier input, while inverting or not inverting an output of the single amplifier depending upon which of the first eye and the second eye is being stimulated.

22. The method according to claim 13, wherein the apparatus is configured to automatically test both the first eye of the patient and the second eye of the patient without requiring intervention by a clinician.

23. The method according to claim 13, wherein the visual stimulus is a pattern display.

24. The method according to claim 23, wherein the pattern display is temporally and/or spatially modulated.

* * * * *